United States Patent [19]

Heyes et al.

[11] 3,997,518
[45] Dec. 14, 1976

[54] 2-ALKYL-4-CARBOXYALKYL-5-(3,3'-DIMETHYLTRIAZENO)-IMIDAZOLES

[75] Inventors: James Heyes, Peaslake; Neal Ward, Walton-on-the-Hill, both of England

[73] Assignee: Beecham Group Limited, Great Britain

[22] Filed: Nov. 27, 1974

[21] Appl. No.: 527,581

Related U.S. Application Data

[63] Continuation of Ser. No. 289,610, Sept. 18, 1972, abandoned, which is a continuation-in-part of Ser. No. 205,345, Dec. 6, 1971, abandoned.

[30] Foreign Application Priority Data

Dec. 9, 1970 United Kingdom ............ 58385/70
Sept. 29, 1971 United Kingdom ............ 45309/71

[52] U.S. Cl. .................... 260/140 R; 260/141; 260/248 AS; 260/309; 424/226
[51] Int. Cl.² ................ A61I 27/00; C07C 115/00
[58] Field of Search ................................ 260/140

[56] References Cited

UNITED STATES PATENTS 3,649,613  3/1972  Krauth et al. .................... 260/140

OTHER PUBLICATIONS

Shealy et al (I), J. Org. Chem., vol. 27, pp. 2150–2154 (1962).
Shealy et al (II), J. Med. Chem., vol. 9, pp. 34–38 (1966).
Shealy et al (III), J. Pharm. Sciences, vol. 56, pp. 147–148 (1967).
Shealy et al (IV), Nature, vol. 210, p. 208 (1966).

*Primary Examiner*—Floyd D. Higel

[57] ABSTRACT

Imidazoles of the formula:

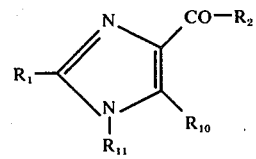

and their salts, wherein $R_1$ is an optically substituted hydrocarbon, heterocyclic or thiol group; $R_2$ is an amino or optionally substituted etherified hydroxyl group; $R_{11}$ is a negative charge or alkyl group when $R_{10}$ is $N_2+$ or $R_{11}$ is a hydrogen atom or alkyl group when $R_{10}$ is $N=N-NR_3R_4$ where $R_3$ is methyl or $\beta$-chloroethyl and $R_4$ is optionally substituted hydrocarbon. When $R_{10}$ is $N_2+$ the compounds are useful as intermediates in the synthesis of compounds wherein $R_{10}$ is $N=N-NR_3R_4$ these latter compounds possessing antitumor and/or anti-microbial activity.

4 Claims, No Drawings

2-ALKYL-4-CARBOXYALKYL-5-(3,3'-DIMETHYL-TRIAZENO)-IMIDAZOLES

This is a continuation of application Ser. No. 289,610 filed Sept. 18, 1972, and now abandoned which itself is a continuation-in-part of Ser. No. 205,345 filed Dec. 6, 1971, now abandoned.

The present invention relates to novel substituted imidazoles having pharmocodynamic activity and to pharmaceutical compositions containing them.

Triazenoimidazoles of the formula (I)

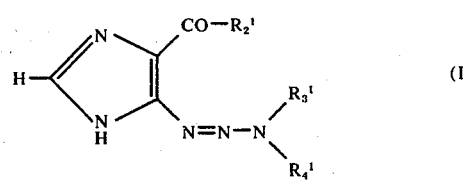

wherein $R_2^1$ is an amino or alkoxyl group, $R_3^1$ is an optionally substituted alkyl group and $R_4^1$ is a hydrogen atom or optionally substituted alkyl group are known to possess biological activity. A comprehensive review of compounds of formula (I) and their biological activities is given by Y. Fulmer Shealy in the Journal of Pharmaceutical Sciences, 11, 1533 (1970).

Certain compounds of formula (I) wherein $R_2^1$ is an alkoxyl group are disclosed and claimed in U.S. Pat. No. 3,649,613 wherein they are stated to have utility as sanitizing agents because of their antimicrobial activity.

Although many variations of compounds of formula (I) have been made, all have retained the hydrogen atom at the 2-position of the imidazole ring. Possibly this was because it was thought that no fundamental change should be made in the structure of the imidazole ring without loss of activity resulting from the departure from structural similarity to the naturally occurring purine precursors and in particular to 5-aminoimidazole-4-carboxamide (AIC) which is also a precursor of the compounds of formula (I).

Throughout his review Y. Fulmer Shealy frequently reminds the reader that compounds of formula (I) are closely related to AIC. Again one of the most successful anti-tumour compounds reported within general formula (I) is that wherein $R_2^1$ is an amino group and $R_3^1$ and $R_4^1$ are methyl the resulting compound being known as dimethyltriazeno imidazole carboxamide (DIC).

The close structural relationship between DIC and AIC is commented upon by Skibba et al. [Biochemical Pharmacology, 19, 2043 (1970)] where it is stated that in man, the anti-tumour compound DIC is degraded substantially to AIC.

Compounds of formula (I) tend to be unstable in solution especially those in which $R_2^1$ is an amino groups (II). Such compounds tend to undergo decomposition reactions such as loss of $HNR_4R_5$ to yield diazo compound (III) followed by further reaction to a 2-azahypoxathine (IV):

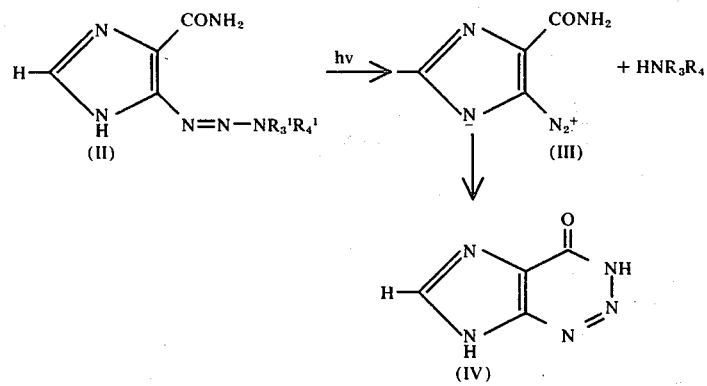

Compounds of formula (I) are synthesised by the reaction of an amine $HNR_3^1R_4^1$ and a diazo compound (V)

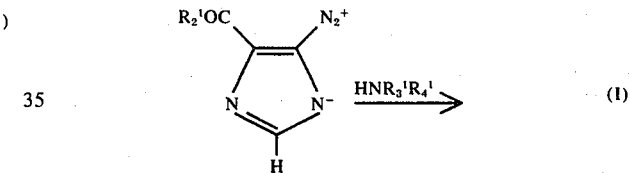

A disadvantage of such a method of synthesis is that the diazo compounds (V) are unstable and tend to lose nitrogen in the manner similar to that of non-aromatic diazonium ions so that yields of the desired triazeno compound are often low.

Thus the objects of the present invention include providing pharmacologically active triazenoimidazoles having one or more advantages selected from greater stability, greater ease of synthesis, greater pharmacologically activity or lower mammalian toxicity than previously known triazeneoimidazoles.

Surprisingly, we have found that it is possible to depart from the AIC structure and retain or even enhance pharmacological activity and in some instances produce compounds of lower mammalian toxicity, stability, or greater ease of synthesis.

Accordingly, the present invention provides compounds of formula (VI):

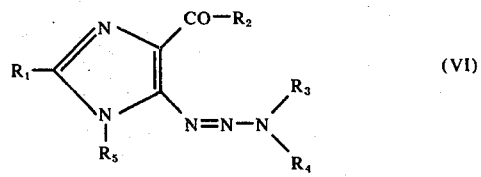

wherein $R_1$ is an optionally substituted hydrocarbon group of 1-20 carbon atoms, an optionally substituted heterocyclic group containing 5- or 6- atoms in the heterocyclic ring or an optionally substituted thiol group; $R_2$ is an amino or optionally substituted etherified hydroxyl group; $R_3$ is a methyl or $\beta$-haloethyl group; $R_4$ is an optionally substituted hydrocarbon group of 1–20 carbon atoms; $R_5$ is a hydrogen atom or alkyl group of 1 to 6 carbon atoms; and isomers or salts and/or hydrates thereof Tautomeric forms of compounds (VI) exist when $R_5$ is H and may be exemplified by the structures (VIa) and (VIb):

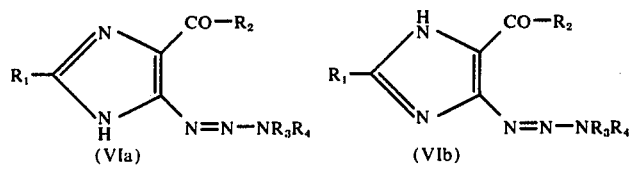

Isomers of compounds (VI) exist when $R_5$ is an alkyl group and may be exemplified by structures (VIc) and (VId)

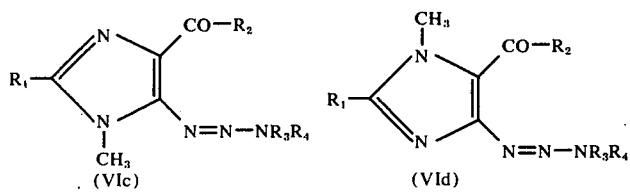

Isomers of compound (VI) about the N=N double bond may exist and may be exemplified by structures (VIe) – (VIf) (This form of isomerism is not thought to be important to activity):

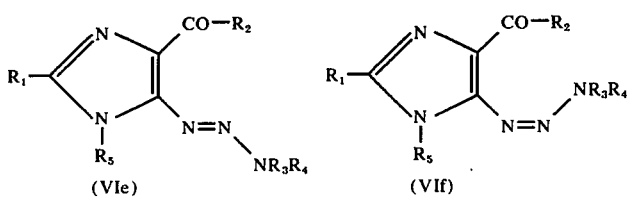

Salts include pharmaceutically acceptable non-toxic acid addition salts. Preferred salts include those of inorganic acids such as the hydrohalic, sulphuric or phosphoric acids and organic acids such as acetic or citric acid.

Suitably $R_1$ may be a thiol, alkylthiol, arylthiol or an optionally substituted aliphatic, alicyclic, carbocylic aromatic or 5- or 6- membered heterocyclic group containing one, two, three or four ring heteroatoms.

Suitable alkyl thiol groups include the methyl thiol, ethyl thiol and benzylthiol groups. Suitable aryl thiol groups include the phenyl thiol and tolylthiol groups.

Suitable optionally substituted aliphatic groups include the methyl, ethyl, n-propyl, iso-propyl, pentyl, hexyl, phenylethyl, hydroxymethyl, methoxymethyl, benzyloxymethyl, chloromethyl, benzyl, p-fluorobenzyl, phenoxymethyl, carboethoxymethyl and like groups.

Suitable optionally substituted alicyclic groups include the cyclopentyl, cyclohexyl, methylcyclohexyl and like groups.

Suitable optionally substituted carbocyclic aromatic groups include the phenyl naphthyl, monohalophenyl, dihalophenyl, toluyl, nitrophenyl, alkylphenyl, alkoxyphenyl, hydroxyphenyl, acyloxyphenyl, phenylphenyl, dialkylaminophenyl, acylaminophenyl, aminophenyl, trifluoromethyl, carboxyphenyl, carboxyalkylphenyl, dialkoxyphenyl and like groups.

Suitable optionally substituted heterocyclic aromatic groups include the pyridyl, thienyl, thiazolyl, furyl, nitrothienyl and like groups.

Preferred groups $R_1$ include the phenyl, fluorophenyl chlorophenyl, dichlorophenyl, nitrophenyl, thienyl, methyl, ethyl, benzyl, 2-phenylethyl, phenoxymethyl, carboethoxymethyl, methoxymethyl, methylthiol, and like groups.

Suitable groups $R_2$ include the amino group, the hydroxy group substituted by a $C_{1-12}$ hydro-carbon groups which may be aliphatic, alicyclic, aryl or araliphatic group of any of which may be substituted by one or more halogen atoms or optionally alkylated or acylated hydroxyl groups of optionally mono- or di-alkylated or acylated amino groups.

Preferred groups $R_2$ include the amino, methoxyl, ethoxyl, propoxyl and like groups of 1 to 7 carbon atoms.

Suitable Groups $R_3$ include the methyl 2-chloroethyl and like groups.

Preferably $R_3$ is a methyl group.

Suitable groups $R_4$ include the methyl, ethyl, propyl, butyl, benzyl, phenyl, cyclohexyl, 2-chloroethyl, 2-hydroxymethyl and like groups.

Preferably $R_4$ is a methyl group.

Suitable groups $R_5$ include the hydrogen atoms, methyl ethyl, hexyl and like groups.

Preferably $R_5$ is a hydrogen atom.

An especially preferred group of compounds of formula (VI) are those of formula (VII):

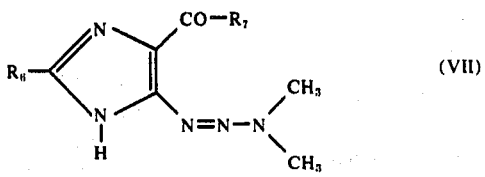

and salts and tautomers thereof wherein $R_6$ is a methyl, ethyl, phenyl or methylthiol groups, $R_7$ is an amino, methoxyl or ethoxyl group.

Compounds of formula (VI) may be prepared by the reaction of an amine $HNR_3R_4$ and a diazo compound of the appropriate formula (VIII):

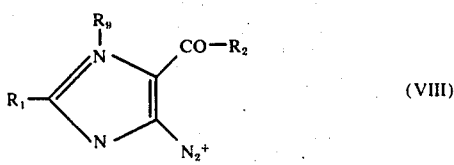

wherein $R_9$ is a negative charge or a $C_{1-6}$ alkyl group. When $R_9$ is an alkyl group an external cation is present such as chloride, bromide, fluoroborate and the like.

Generally an excess of the amine is used, the reaction taking place in a solvent medium such as an optionally aqueous alcohol such as methanol or ethanol or an ether solvent such as diethyl ether or tetrohydrofuran or a chlorinated hydrocarbon solvent such as chloroform.

The reaction may take place at low, ambient or elevated temperatures, the temperature selected generally depending on the stability of the diazo compound (VIII).

When the diazonium ion is relatively stable, for example, when $R_8$ is a negative charge and $R_1$ is an aromatic system, a suitable temperature range for the reaction is $-20°-120°$ C, preferably $0°-80°$ C, most preferably at room temperature.

If the diazonium ion is relatively unstable, for example, when $R_8$ is an alkyl group, then depressed temperatures are generally most efficient, a suitable temperature range being $-20°$ to $20°$ C, preferably at approximately $0°$ C.

If the diazonium is of intermediate stability, for example, as when $R_8$ is a negative charge and $R_1$ is an alkyl group, the reaction may take place at low or ambient temperatures, for example, $-20°-80°$ C, preferably $0°-40°$ C, most preferably at room temperature.

The diazo compounds of formula (IV) may be prepared from compounds of formula (V):

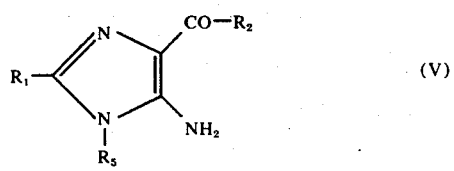

by reaction with nitrous acid or a nitrite salt or ester or the like in the presence of an acid capable of liberating nitrous acid from the said salt or ester.

The reaction is normally carried out in water although other solvents such as optionally aqueous alcohols or the like may be used if desired.

Suitable nitrite salts include the sodium and potassium salts and the like, the sodium nitrite salt being preferred.

Suitable acids include mineral acids such as sulphuric, nitric, hydrohalic, fluoroboric, and like acids or organic acids such as acetic, formic or like acids. Hydrochloric acid is generally preferred.

The reaction temperatures used depends upon the nature of the groups $R_1$ and $R_5$ in a manner analogous to that described for the amination of the diazonium ion. Thus if $R_5$ is an alkyl group depressed temperatures are used, for example, $-5°-0°$ C, while higher temperatures may be used if $R_5$ is a hydrogen atom, for example $0°-40°$ C depending on the nature of $R_1$. In this latter case, generally if $R_1$ is an aromatic group the reaction is carried out at room temperature without cooling but if $R_1$ is a non-aromatic group, care should be taken that the reaction temperature does not rise above $20°$ C, preferably not above $15°$ C.

The diazo compounds of formula (VIII) are frequently insoluble in water and are precipitated as they are formed. Thus they may be filtered off and, if desired purified by recrystallization from an appropriate solvent such as ethanol, cyclohexane or the like. Those salts that are water soluble may, if required be extracted with a water immiscible solvent such as chloroform in conventional manner.

An alternative process that may be used is to add an acid solution of the aminoimidazole to one equivalent of an aqueous solution of a nitrite salt; this helps minimise side reactions.

Compounds of formula (V) may be prepared by the methods described in the aforementioned article by Y. Fulmer Shealy, a particularly flexible method synthesis of the compounds being that of Shaw et.al. [Journal of the Chemical Society, 1962 (1941)] which method comprises the reaction of an α-amino nitrile of the formula (IX)

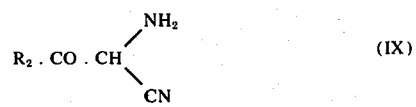

with a benzylthioformamino hydrochloride of the formula (X):

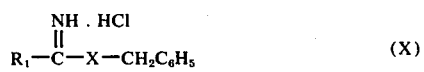

in an aprotic solvent at an elevated temperature such a reaction is described in Example 1 herein. Further details of the preparation of the amino-imidazoles may be found in West German Offenlegungsschriften Nos. P2142831 and P2142832.

Compounds of formula (V) wherein $R_5$ is an alkyl group may be prepared by the alkylation of the corresponding compounds wherein $R_5$ is hydrogen, by methods known per se.

The invention also provides a method of treating cancer in mice and dogs. According to this aspect of the invention, mice and dogs may be treated with a therapeutic composition containing a compound of formula (VI). Such compositions may be administered by any convenient route, oral administration and administration as injection being preferred.

Generally treatment requires that the mouse and dog be dosed with the compound on repeated occasions, for example, once or more times a day for 10 days or more. Alternatively, the compound may be administered over a prolonged period at infrequent intervals, for example, once a month for 6 months.

The compound may be the sole anti-tumour agent used or it may be used together with or alternating with other anti-tumour agents.

In general the compound will be administered in doses of between 0.2 mg/kg and 200 mg/kg, preferably between 1 mg/kg and 50 mg/kg.

Thus the useful novel compounds provided by this invention are of the pharmaceutically beneficial compounds of formula (VI) and the useful intermediates of formula (VIII) as defined herein. Hence the sum of novel compounds presented by this invention may be represented by the formula (XI):

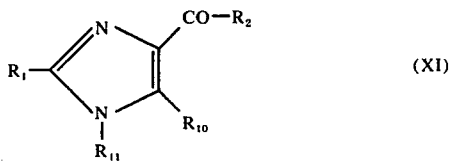

(XI)

wherein $R_1$ is an optionally substituted hydrocarbon group of 1–20 carbon atoms, an optionally substituted heterocyclic group containing 5- or 6- atoms in the heterocyclic ring, an optionally substituted thiol group; $R_2$ is an amino or optionally substituted etherified hydroxyl group; $R_{11}$ is a negative charge or a $C_{1-6}$ alkyl group when $R_{10}$ is a $N_2^+$ group or $R_{11}$ is a hydrogen atom or a $C_{1-6}$ alkyl group when $R_{10}$ is a $N=N-NR_3R_4$ group where $R_3$ is a methyl or $\beta$-chloroethyl group; $R_4$ is an optionally substituted hydrocarbon group of 1–20 carbon atoms, and tautomers, isomers or salts and hydrates thereof.

The following Examples illustrate the processes used to prepare the compounds of the invention and the biological activities of some of the compounds.

In the Examples temperatures are given throughout in ° C.

The structure of all compounds was checked by standard i.r. and n.m.r. techniques. All diazo compounds were seen to have a characteristic absorption band at about 2160 cm$^{-1}$, all triazenes were seen to have a characteristic absorption band at about 1080 cm$^{-1}$. The methyl groups of all 3,3-dimethyltriazenes had a resonance integrating to 6 protons at about $\delta = 3.3$.

EXAMPLE 1

5-Amino-4-carbethoxy-2-phenylimidazole hydrochloride

Phenylformimino benzyl thioether hydrochloride (28.5gm) was refluxed in chloroform (200 ml) with ethyl aminocyanoacetate (17.0gm) for 1 hour. On standing for 8 hours the addition of dry diethyl ether (250 ml) caused the precipitation of the 5-amino-4-carbethoxy-2-phenylimidazole hydrochloride (24.5gm) m.p. 228° C after recrystallisation from ethanol.

Other 5-aminoimidazoles used in the following Examples were normally prepared in an analogous manner.

EXAMPLES 2–30

EXAMPLE 2

4-Carbethoxy-5-diazo-2-phenylimidazole

4-Amino-5-carbethoxy-2-phenylimidazole hydrochloride (37.0gm) was suspended in water (750 mls) containing sodium nitrite (15gm) and the mixture stirred at room temperature.

A solution of 2N hydrochloric acid (100 ml) was added in portions over five minutes and the mixture stirred 1 hour. The yellow product was collected, washed with water and dried in vacuo to give 31.4 gm of crude diazo compound.

Recrystallisation from ethanol/water gave 26.3gm of the pure 4-carbethoxy-5-diazo-2-phenyl imidazole mp 111° C (with decomposition). The product was soluble in organic solvents such as diethyl ether or chloroform and showed the characteristic diazo band in the infrared spectrum at about 2160 cm$^{-1}$.

Using the method of Example 2 compounds of the formula

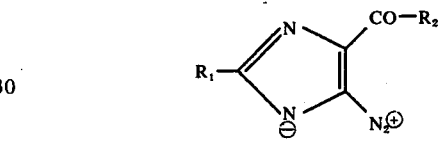

were prepared.

| Ex. | $R_1$ | $R_2$ | mp° C (with Decomposition) |
|---|---|---|---|
| 3 | $C_6H_4F(p)$ | $OC_2H_5$ | 122 |
| 4 | $C_6H_4NO_2(p)$ | $OC_2H_5$ | 200 |
| 5 | 3-thienyl | $OC_2H_5$ | 117 |
| 6 | 2-thienyl | $OC_2H_5$ | 131 |
| 7 | 5-nitro-2-furyl | $OC_2H_5$ | 183 |
| 8 | $C_6H_5$ | $OCH_2C_6H_4Cl(p)$ | 119 |
| 9 | $C_6H_5$ | $OCH_2C_6H_5$ | 126 |
| 10 | $C_6H_4F(o)$ | $OC_2H_5$ | 108 |
| 11 | $C_6H_5$ | $OCH_2CH_2CH_3$ | 88 |
| 12 | $C_6H_5$ | $OCH(CH_3)_2$ | 96 |
| 13 | $C_6H_5$ | $NH_2$ | 290 |
| 14* | SH | $OC_2H_5$ | 102 |
| 15* | $CH_2C_6H_4$ | $OC_2H_5$ | 91 |
| 16 | $CH_2C_6H_5Cl(p)$ | $OC_2H_5$ | 92 |
| 17 | $CH_2OC_6H_5$ | $OC_2H_5$ | 89 |
| 18 | $CH_2C_6H_5$ | $OC_2H_5$ | 47 |
| 19 | $CH_3$ | $OC_2H_5$ | 56 |
| 20 | $CH_3$ | $NH_2$ | 178** |
| 21 | $CH_2OC_6H_5OCH_3(p)$ | $OC_2H_5$ | 135–135.5 |
| 22 | $CH_2CO_2C_2H_5$ | $OC_2H_5$ | |
| 23 | $C_3H_5$ | $OC_2H_5$ | |
| 24 | $CH_2CH_2C_6H_5$ | $OC_2H_5$ | |
| 25 | n-$C_7H_{15}$ | $OC_2H_5$ | |
| 26 | $SCH_2C_6H_5$ | $OC_2H_5$ | |
| 27* | SH | $NH_2$ | |

Examples marked thus * were prepared in the dark.
**m.p. 178° on rapid heating, 60° on slow heating.

EXAMPLES 28 – 70

EXAMPLE 28

4-Carbethoxy-5-(3,3-dimethyl-triazeno)-2-phenyl imidazole

A solution of 4-carbethoxy-5-diazo-2-phenylimidazole (8.0 gm) in methanol (75 ml) was treated with a 30% solution of dimethylamine in methanol (25 ml). The mixture was diluted with water to give the product as a pale yellow crystalline solid. This was collected, washed with water and dried in vacuo to yield 4-carbethoxy-5-(3,3-dimethyl-triazeno) -2-phenyl imidazole, 8.22g. A sample recrystallised from methanol/water yielded a pure product, mp 171° C.

EXAMPLE 29

4-Carbethoxy-5-(3,3-dimethyltriazeno)-2-(p-fluorophenyl) imidazole

4-Carbethoxy-5-amino-2-(p-fluorophenyl) imidazole hydrochloride (2.0g) was suspended in water (20 ml) containing sodium nitrite (1.0g). The mixture was stirred at room temperature and 1N hydrochloric acid (25 ml) added slowly. The mixture was stirred for 10 minutes and extracted with chloroform (25 ml). The phases were separated, the aqueous phase extracted with a further portion of chloroform (25 ml) and the combined chloroform solutions washed with saturated sodium chloride solution (25 ml). A solution of dimethylamine in ethanol (7 ml of a 25% solution) was added and the mixture evaporated to yield the crude product. This was recrystallised from ethanol/water to yield 4-carbethoxy-5-(3,3-dimethyltriazeno)-2-(p-fluorophenyl)imidazole, 1.55g, m.p. 177° C with decomposition.

EXAMPLE 30

4-Carbethoxy-5-(3,3-dimethyltriazeno)-2-methylimidazole

To 4-Carbethoxy-5-diazo-2-methylimidazole (4.73g.) in chloroform (30 ml.) was added a 33% w/w solution of dimethylamine in ethanol (9.5 ml.) and the mixture stirred at room temperature for 2 hours. The solution was concentrated under low pressure to approximately 20% of its previous volume; this was diluted with diethyl ether which was filtered off and washed with further diethyl ether to yield 5.5g. of crude, light brown product. The solid was recrystallised from ethyl acetate to yield as a powder 3.17g. (53.5%) of an off white 4-carbethoxy-5-(3,3-dimethyltriazeno)-2-methyl-imidazole, m.p. 120° (dec).

Compounds of the formula

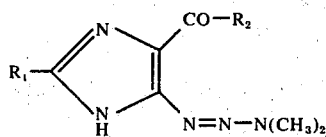

were prepared by the general methods analogous to those of Examples 28–30

| Ex. | $R_1$ | $R_2$ | mp° C (with decompositon) |
|---|---|---|---|
| 31 | $C_6H_4Cl(p)$ | $OC_2H_5$ | 144 |
| 32 | $C_6H_4CF_3(p)$ | $OC_2H_5$ | 175 |
| 33 | $C_6H_4CH_3(p)$ | $OC_2H_5$ | 177 |
| 34 | $C_6H_4NO_2(p)$ | $OC_2H_5$ | 176 |
| 35 | $C_6H_4OCH_3(p)$ | $OC_2H_5$ | 168 |
| 36 | $C_6H_4OCH_2C_6H_5(p)$ | $OC_2H_5$ | 168 |
| 37 | $C_6H_4-C_6H_5(p)$ | $OC_2H_5$ | 175 |
| 38 | $C_6H_4CH_3(m)$ | $OC_2H_5$ | 176 |
| 39 | $C_6H_4F(m)$ | $OC_2H_5$ | 177 |
| 40 | $C_6H_4F(o)$ | $OC_2H_5$ | 130 |
| 41 | $C_6H_3(OCH_3)_2(3,4)$ | $OC_2H_5$ | 180 |
| 42 | $C_6H_3Cl_2(3,5)$ | $OC_2H_5$ | 183 |
| 43 | 2-thienyl | $OCH_5$ | 173 |
| 44 | 3-thienyl | $OC_2H_5$ | 178 |
| 45 | 2-furyl | $OC_2H_5$ | 148 |
| 46 | 4-thiazolyl | $OC_2H_5$ | 171 |
| 47 | β-naphthyl | $OC_2H_5$ | 194 |
| 48 | $C_6H_5$ | $OCH_3$ | 181 |
| 49 | $C_6H_5$ | $OCH_2CH_2CH_3$ | 167 |
| 50 | $C_6H_5$ | $OCH(CH_3)_2$ | 165 |
| 51 | $C_6H_5$ | $OCH_2C_6H_5$ | 88 (monohydrate) |
| 52 | $C_6H_5$ | $OCH_2C_6H_4Cl(p)$ | 155 |
| 53 | $C_6H_5$ | $OCH_2CH_2Cl$ | 166 |
| 54 | $C_6H_5$ | $NH_2$ | 178 |
| 55 | $C_6H_4Cl(p)$ | $NH_2$ | 170 (broad) |
| 56 | 2-thienyl | $NH_2$ | 193 (broad) |
| 57 | $CH_2CO_2C_2H_5$ | $OC_2H_5$ | 109 |
| 58 | $C_2H_5$ | $OC_2H_5$ | 151.5 |
| 59 | $SCH_2C_6H_5$ | $OC_2H_5$ | 118.5 |
| 60 | $C_6H_5$ | $OCH_3$ | 181 |
| 61 | $CH_2OC_6H_4OCH_3(p)$ | $OC_2H_5$ | 151.5 |
| 62 | $CH_3$ | $NH_2$ | 197 |
| 63 | $CH_2C_6H_5$ | $OC_2H_5$ | 142 (½ hydrate) |
| 64 | HS | $OC_2H_5$ | 205.5 |
| 65 | $CH_2C_6H_5$ | $OC_2H_5$ | 174 (½ hydrate) |
| 66 | $CH_2OC_6H_5$ | $OC_2H_5$ | 151.5 |
| 67 | $n-C_7H_{15}$ | $Oc_2H_5$ | 81.5 |
| 68 | $CH_2C_6H_5$ | $OC_2H_5$ | 80 (broad) |
| 69 | $CH_2C_6H_4Cl(p)$ | $OC_2H_5$ | |
| 70 | SH | $NH_2$ | 151 (½ hydrate) |
| 71 | $n-C_4H_9$ | $OC_2H_5$ | 82 (hydrate) |
| 72 | $i-C_4H_9$ | $OC_2H_5$ | 124 (hydrate) |
| 73 | $c-C_6H_{13}$ | $OC_2H_5$ | 116 (½ hydrate) |
| 74 | $n-C_3H_7$ | $OC_2H_5$ | 133.5 |
| 75 | $SC_2H_5$ | $OC_2H_5$ | 130 |
| 76 | $SCH_3$ | $OCH_3$ | 144 |

EXAMPLE 77–83

EXAMPLE 77

4-Carbethoxy-5-(3-methyl-3-β-hydroxyethyl)triazeno-2-phenyl imidazole

4-Carbethoxy-5-diazo-2-phenyl imidazole (4.84gm) in methanol (100 ml) was treated with a small excess of N-methyl ethanolamine. The mixture was diluted with petrol (60°–80°) until cloudy, and the product allowed to crystallize. 4-Carbethoxy-5-(3-methyl-3-β-hydroxyethyl)triazeno-2-phenyl imidazole was collected and recrystallised from ethyl acetate. The yield was 4.70 g. mp 158° with decomposition.

Compounds of the formula

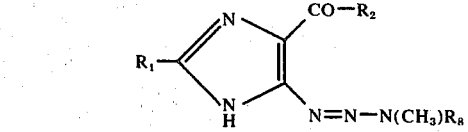

were prepared by methods analogous to that described in Example 77.

| Example | $R_1$ | $R_2$ | $R_8$ | mp (with decomposition) |
|---|---|---|---|---|
| 78 | $C_6H_5$ | $OC_2H_5$ | $C_6H_5$ | 167 |
| 79 | $C_6H_5$ | $OC_2H_5$ | $CH_2C_6H_5$ | 140 |
| 80 | $C_6H_5$ | $OC_2H_5$ | $CH_2CH_2CH_2CH_3$ | 118 |
| 81 | $C_6H_5$ | $OC_2H_5$ | cyclo $C_6H_{11}$ | 132 |
| 82 | $CH_2OC_6H_5$ | $OC_2H_5$ | $CH_2C_6H_5$ | 93 (monohydrate) |
| 83 | $CH_3$ | $NH_2$ | $n-C_4H_9$ | |

EXAMPLE 84

2-Benzyl-5-carbethoxy-(3,3-dimethyltriazeno)-1-methylimidazole

4-Amino-2-benzyl-5-carbethoxy-1-methyl-imidazole (30g.) was suspended in water (12 ml.) containing conc. HCl — (12 ml) and a solution of sodium nitrite (0.96 g.) in water (5 ml.) slowly added with stirring at 0° C. After addition was complete this solution was added to a stirred solution of $Na_2CO_3$ (118 ml, 30%) and aqueous dimethylamine (2.5 ml, 25%) added dropwise at 0° C added with stirring. After half an hour the brown precipitate was filtered off, washed with water and dried. Crystallisation from ethylacetate/petrol yielded 2-benzyl-5-carbethoxy-(3,3-dimethyltriazeno)-1-methylimidazole (1g, 27%) m.p. 107°–108° C (dec).

EXAMPLE 85

4-Carbethoxy-5-(3,3-dimethyltriazeno)-2-(3-pyridyl)imidazole

4-Carbethoxy-5-amino-2-(3-pyrieyl)imidazole hydrochloride (1.90 gm) was dissolved in 5N hydrochloric acid (10 mls) and the mixture stirred at room temperature. A solution of sodium nitrite (0.5 gm) in water (5 ml) was then added in small portions, and the resulting clear solution stirred for 5 minutes. The mixture was then poured into a vigorously stirred mixture of 30% aqueous dimethylamine (1.0 ml) and 10% aqueous sodium carbonate (20 mls) giving a pale brown precipitate. The crude product was recrystallised from methanol/ether to give 0.65 gm of an off-white solid mp. 125° with decomposition.

EXAMPLE 86

4-Carbethoxy-5-(3,3-dimethyltriazeno)-2-p-hydroxyphenyl imidazole

A solution of 4-carbethoxy-5-(3,3-dimethyltriazeno)-2-p-benzyloxyphenyl imidazole (0.50 gm) in methanol (50 ml) was saturated with carbon dioxide, and 10% palladium on charcoal (100 mg) added. The mixture was hydrogenated at room temperature and pressure. Hydrogen (40 ml) was rapidly absorbed (4 minutes). The mixture was filtered and the filtrate evaporated to give a green residue. The product was dissolved in hot methanol, treated with charcoal and precipitated by the addition of 60–80 petrol, as a light brown powder, mp 192° (with decomposition), yield 170 mgs. The NMR Spectrum confirmed the retention of the dimethyltriazeno function, while showing the complete removal of the benzyl protecting group.

EXAMPLE 87

Hydrochloride salt of 4-carbethoxy-5-(3,3-dimethyltriazeno)-2-phenyl imidazole 4-Carbethoxy-5-(3,3-dimethyltriazeno)-2-phenyl imidazole (47.4 gm) was stirred in methanol (500 ml) at room temperature, and concentrated hydrochloric acid (20 ml) added, giving a clear solution. The well stirred mixture was diluted with anhydrous ether (4 liters) and the product slowly crystallised. It was collected, washed well with ether and dried in vacuo, to yield 52.0 gm of an off-white solid, mp. ca 125° with decomposition. It contained one molecule of water of crystallisation.

EXAMPLE 88

Monohydrate of 4-carbethoxy-5-(3,3-dimethyltriazeno)-2-phenyl imidazole

4-Carbethoxy-5-(3,3-dimethyltriazeno)-2-phenyl imidazole (10.0 gm) was stirred at room temperature in pH 7.0 phosphate buffer. The initial lemon-yellow colour slowly faded, and after 3 hours the mixture was almost colourless. The product was collected, washed with water and dried in vacuo over phosphorous pentoxide. The yield was 10.40 gm. The water was removed only very slowly by drying over phosphorous pentoxide.

The product was compared with the anhydrous material by infra-red spectra. The following characteristic peaks were observed in $cm^{-1}$.

| (nujol mulls) | | (C=O) | | (Triazine) |
|---|---|---|---|---|
| anhydrous | — | 1710 | — | 1080 |
| monohydrate | 3250, | 1650, | 1130, | 1080 |

The melting points and NMR spectra were unaffected by monohydrate formation.

EXAMPLE 89

5-Carbethoxy-4-(3,3-dimethyltriazeno)-1-methyl-2-phenyl imidazole

4-Amino-5-carbethoxy-1-methyl-2-phenyl imidazole (2.84) [made by the method of Cook et. al, Journal of the Chemical Society, 1950 (2775)] in 5N hydrochloric acid (24.0 ml) was cooled to 0° C and a cold solution of sodium nitrite (0.96 gm) in water (5 ml) added slowly, with stirring, keeping the mixture at 0° C. The resulting solution was added dropwise to a cold (0° C) mixture of sodium carbonate (120 mls of 30%) and dimethylamine (2.5 mls of 25% aqueous solution).

The product was separated as a gum, which was triturated with a mixture of petrol and diethyl ether to give a light brown solid. The yield was 1.7 gm, mp 79° with decomposition.

EXAMPLE 90

Activity against R1 lymphoma

The R1 lymphoma is normally sensitive to antimetabolites. Typically mice having a transplant of 1.5 × $10^6$ tumour cells die from the metastisizing tumour on day 9, 10 or 11 after transplant.

The compounds illustrated below were dosed by the intra peritoneal route in a vehicle of 10% acetone in arachas oil daily from day 3 to day 7 after tumour transplant. The increase in survival time over control was measured.

The dose reported is that dose which gave the maximum increase in survival time. Lower doses gave less activity and higher doses are toxic.

Methotrexate is a well known anti-tumour agent thought to act as an antimetabolite. Although widely used methotrexate has the disadvantage of high toxicity.

The results are split into two sections (in Table A and Table B) because two slightly different strains of R1 lymphoma were used.

TABLE A

| Compound | Dose mg/kg | Medium % increase in survival time. |
|---|---|---|
| Control | 0 | 0 |
| 4-Carboxamido-5-(3,3-dimethyl-triazeno)-2-phenylimidazole | 50 | 80 |
| 4-Carboxymethyl-5-(3,3-dimethyl triazeno)-2-phenylimidazole | 16 | 400 |
| 4-Carboxyethyl-5-(3,3-dimethyl triazeno)-2-phenylimidazole | 32 | 300 |
| 4-Carboxamido-5-(3,3-dimethyl triazeno)-2-(2-thienyl)imidazole | 128 | 50 |
| 4-Carboxyethyl-5-(3-methyl-3-benzyltriazeno)-2-(4-chlorophenyl)imidazole. | 100 | 40 |
| 4-Carboxyethyl-5-(3,3-dimethyl triazeno)-2-(4-methoxyphenyl) imidazole. | 33 | 50 |
| 4-Carboxyethyl-5-(3,3-dimethyl triazeno)-2-(3-methyl-phenyl) imidazole. | 128 | 150 |
| 4-Carboxyethyl-5-(3,3-dimethyl triazeno)-2-(2-fluorophenyl) imidazole. | 10 | 100 |
| 4-Carboxyethyl-5-(3,3-dimethyl triazeno)-2-(3,4-dimethoxy-phenyl)imidazole. | 33 | 200 |
| 4-Carboxyethyl-5-(3,3-dimethyl triazeno)-2-(2-naphthyl) imidazole. | 128 | 170 |
| 4-Carboxyethyl-5-(3,3-dimethyl triazeno)-2-(3-thienyl) imidazole. | 33 | 200 |
| 4-Carboxyethyl-5-(3,3-dimethyl triazeno)-2-(3-pyridyl) imidazole. | 32 | 170 |
| 4-Carbethoxy-5-(3,3-dimethyl triazeno)-2-carbethoxymethyl imidazole. | 64 | 400 |
| 4-Carbethoxy-5-(3,3-dimethyl triazeno)-2-p-methoxy-phenoxymethylimidazole. | 64 | >150 |
| 4-Carbethoxy-5-(3,3-dimethyl triazeno)-2-phenoxymethyl imidazole. | 64 | 85 |
| 4-Carbethoxy-5-(3,3-dimethyl-triazeno)-2-benzyl imidazole. | 64 | 200 |
| Methotrexate (4-amino-10-methyl folic acid) | 2 | 100 |
| DIC | 32 | 300 |

TABLE B

| Compound | Dose mg/kg | Medium % increase in survival time. |
|---|---|---|
| 4-Carbethoxy-5-(3,3-dimethyl triazeno)-2-mercapto imidazole. | 128 | 140 |
| 4-Carbethoxy-5-(3,3-dimethyl triazeno)-2-phenyl imidazole. | 33 | 65 |
| 4-Carbethoxy-5-(3,3-dimethyl triazeno)-2-methylmercapto imidazole. | 64 | 67 |
| 4-Carbethoxy-5-(3,3-dimethyl triazeno)-2-methyl imidazole. | 32 | 90 |
| 4-Carbethoxy-5-(3,3-dimethyl triazeno)-2-n propyl imidazole. | 32 | 130 |
| 4-Carbethoxy-5-(3,3-dimethyl triazeno)-2-ethyl imidazole. | 32 | 70 |
| 4-Carbethoxy-5-(3,3-dimethyl triazeno)-2-cyclohexyl imidazole. | 21 | 85 |
| 4-Carboxamido-5-(3,3-dimethyl triazeno)-2-methyl imidazole. | 128 | 60 |
| 4-Carbethoxy-5-(3,3-dimethyl triazeno)-2-dimethylamino imidazole. | 16 | 45 |
| 4-Carbmethoxy-5-(3,3-dimethyl triazeno)-2-mercapto imidazole. | 32 | 90 |
| 4-Carbethoxy-5 (3,3-β-chloroethyl triazene)-2-phenyl imidazole. | 128 | 35 |

TABLE B-continued

| Compound | Dose mg/kg | Medium % increase in survival time. |
|---|---|---|
| 4-Carbethoxy-5-3,3-dimethyl triazeno-2-methylmercapto imidazole. | 64 | 100 |
| 4-Carbethoxy-5-(3,3-dimethyl triazeno-1-2 dimethyl imidazole. | 32 | 65 |
| Methotrexate (4-amino-10-methyl folic acid) | 2 | 60 |
| D.I.C. | 33 | 60 |

EXAMPLE 91

The breadth of antitumour spectrum of the compounds of the invention in mice is illustrated by their activity in the ADJ/PC6 plasma cell tumour. This is a solid tumour sensitive to most alkylating agents. Good activity is rarely seen against this tumour and the R1 lymphoma. The percentage inhibition of tumour weight is compared with controls and the therapeutic index shows the dose at which 90% inhibition occurs ($ID_{90}$) compared with the dose at which 50% of the animals were killed ($LD_{50}$).

| Compound | Dose i.p. dosing × 5 | | Therapeutic Index. |
|---|---|---|---|
| | $LD_{50}$ | $ID_{90}$ | |
| 4-Carboxamido-5-(3,3-dimethyltriazeno)-2-phenylimidazole. | 240mg/kg | 16.0mg/kg | 15 |
| 4-Carboxyethyl-5-(3,3-dimethyltriazeno)-2-phenylimidazole. | 310mg/kg | 3.5mg/kg | 88 |
| 4-Carboxyethyl-5-(3,3-dimethyltriazeno)-2-(4-fluorophenyl) imidazole. | 200mg/kg | 20mg/kg | 10 |
| Methotrexate | — | Inactive | — |

EXAMPLE 92

The test of example 91 was repeated using the PC 6 tumour screen.

| Compound | Therapeutic Index. | |
|---|---|---|
| | i.p. dosing | oral dosing |
| 4-Carboxyethyl-5-(3,3-dimethyltriazeno)-2-phenylimidazole. | 27 | 11 |
| 4-Carboxyethyl-5-(3,3-dimethyltriazeno)-2-methylimidazole. | 47 | 40 |
| DIC | 33 | 24 |

EXAMPLE 93

Activity of these compounds has also been shown in Friend Leukaemia. Friend leukaemia virus is a prolonged infection in mice produced splenomegaly. 4-Carboxyethyl-5-(3,3-dimethyltriazeno)-2-phenylimidazole dosed sub-cutaneously at 250 mg/kg/day on day −1, +1, +2 and +3 with respect to infection gave complete inhibition of the splenomegally.

EXAMPLE 94

Certain of the compounds of the invention are less toxic than related previously known compounds. For example, 4-Carboxyethyl-5-(3,3-dimethyltriazeno)-2-phenylimidazole and 4-Carboxamide-5-(3,3-dimethyltriazeno)imidazole (D.I.C.) have been given both by the oral and intravenous route to male and female beagle dogs. The dose regimen was 20mg/kg on day 0, 45 mg on day 4 and a final dose of 90mg/kg given on day 9. 4-Carboxyethyl-5-(3,3-dimethyltriazeno)-2-phenylimidazole dosed orally and intravenously showed no adverse clinical signs, the animals remaining in good health. DIC administered by either route, showed a massive decrease in total circulating white cells and platelets. Oral dosing of DIC with one dog had to be stopped after the second dose. None of these effects were noted with 4-carboxyethyl-5-(3,3-dimethyltriazeno)-2-phenylimidazole at these dose levels.

EXAMPLE 95

Compounds of this invention have shown antibacterial activity. Thus the minimum inhibitory concentration (M.I.C.) of 4-carboxyethyl-5-(3,3-dimethyltriazeno)-2-phenylimidazole and the corresponding 2-methylimidazole in DST agar + 5% lysed horse blood are illustrated against the following bacteria.

| Organism. | MIC in μg/ml | |
| --- | --- | --- |
|  | 2-phenyl compound | 2-methyl compound |
| Streptococus heamolyticus | 1 |  |
| Staphylococus aureus | 10 | 7.5 |
| E. Coli |  | 15 |
| Proteus mirabilis |  | 15 |
| Pseudomonas aeroginosa |  | 62 |

EXAMPLE 96

Antifungal activity has been found in compounds of this invention. Thus 4-carboxyethyl-5-(3,3-dimethyltriazeno)-2-phenylimidazole has the following minimum inhibitory concentrations.

| Candida albicans | 10 μg/ml |
| --- | --- |
| Candida neoformans | 10–50 μg/ml |
| Trychopyton mentagrophytes | 10 μg/ml |

The activity against Candida and related organisms is especially useful in potentially anti-leukaemia agents as secondary micoses, especially due to such organisms, are becoming increasingly important as a contributory cause of death in leukaemia [see J. G. Gruhn, Cancer, 16, 61 (1963)].

What is claimed is:

1. A compound of the formula

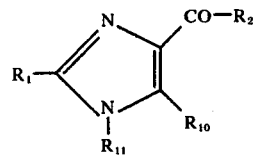

wherein
$R_1$ is methyl;
$R_2$ is alkoxyl of 1 to 4 carbon atoms;
$R_{10}$ is $N=N-N(CH_3)_2$; and
$R_{11}$ is hydrogen;
or a pharmaceutically acceptable, nontoxic acid addition salt or mono-hydrate thereof.

2. A compound according to claim 1 wherein $R_2$ is ethoxyl.

3. The compound according to claim 1 which is 4-carbethoxy-5-(3,3-dimethyltriazeno)-2-methylimidazole.

4. A compound according to claim 1 which is a pharmaceutically acceptable, nontoxic acid addition salt of 4-carbethoxy-5-(3,3-dimethyltriazeno)-2-methylimidazole.

* * * * *